United States Patent [19]

Bartels-Keith, deceased et al.

[11] Patent Number: 4,713,313

[45] Date of Patent: Dec. 15, 1987

[54] PHOTOGRAPHIC SYSTEM AND NOVEL COMPOUNDS

[75] Inventors: James R. Bartels-Keith, deceased, late of Lexington, Mass., by Dorothy F. Bartels-Keith, executrix; Anthony J. Puttick, Arlington; Lloyd D. Taylor, Lexington, both of Mass.

[73] Assignee: Polaroid Corporation, Patent Dept., Cambridge, Mass.

[21] Appl. No.: 606,350

[22] Filed: May 2, 1984

[51] Int. Cl.$^4$ ............................ G03C 5/54; G03C 5/38
[52] U.S. Cl. .................................... 430/251; 430/428; 430/455; 430/566; 544/243; 544/310; 544/311; 544/312
[58] Field of Search ............... 430/251, 455, 428, 234, 430/566; 544/243, 310, 311, 312

[56] References Cited

U.S. PATENT DOCUMENTS

| | | | |
|---|---|---|---|
| 2,857,274 | 10/1958 | Land et al. | 430/251 |
| 2,857,276 | 10/1958 | Land et al. | 430/251 |
| 3,709,690 | 1/1973 | Cohen et al. | 430/213 |
| 4,056,666 | 11/1977 | Seita et al. | 544/312 |
| 4,126,459 | 11/1978 | Greenwald | 430/251 |
| 4,298,675 | 11/1981 | Taylor | 430/213 |
| 4,350,754 | 9/1982 | Bartels-Keith et al. | 430/219 |

*Primary Examiner*—Richard L. Schilling
*Attorney, Agent, or Firm*—Gaetano D. Maccarone

[57] ABSTRACT

Compounds which include a quaternary group connected to a pyrimidine residue through a linkage are disclosed. These compounds are useful as silver halide solvents in photographic products, processes and compositions.

24 Claims, No Drawings

PHOTOGRAPHIC SYSTEM AND NOVEL COMPOUNDS

BACKGROUND OF THE INVENTION

The invention relates to photography and more specifically, is directed to novel compounds which function as silver halide solvents and photographic products, processes and compositions which employ the compounds.

Photographic processing compositions capable of forming water-soluble complex silver salts are known to be useful in many types of siler halide photography. In conventional or "tray" development, it is customary to fix the developed silver halide emulsion by applying a solution of silver halide solvent, i.e., silver halide complexing agent which forms a water-soluble silver complex with the residual silver halide. The water-soluble silver complex thus formed and excess silver solvent are then removed from the developed and fixed emulsion by washing with water.

Silver halide solvents also have been employed in monobaths where a single processing composition containing a silver halide developing agent, in addition to the silver halide solvent, is utilized for both developing and fixing an exposed photosensitive silver halide layer. Silver halide solvents also have been employed in diffusion transfer photographic processes. Such processes are now well known in the art; see, for example, U.S. Pat. Nos. 2,543,181; 2,647,056; 2,983.606; etc. In processes of this type, an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image. In diffusion transfer processes where a silver transfer image is formed, processing is effected in the presence of a silver halide solvent which forms a diffusible complex with the undeveloped silver halide. The soluble silver complex thus formed diffuses to the superposed image-receiving layer where the transferred silver ions are deposited as metallic silver to provide the silver transfer image. In preparing silver prints in this manner, the image-receiving element preferably includes a silver precipitating agent, for example, heavy metal sulfides and selenides as described in U.S. Pat. No. 2,698,237.

The present invention is directed to novel silver halide solvents and their use in photographic products, processes and compositions.

SUMMARY OF THE INVENTION

It is an object of the invention to provide novel compounds which are useful as silver halide solvents in photography.

It is another object to provide compounds which have a quaternary group connected to a pyrimidine residue through a linking group.

It is a further object to provide photographic products, processes and compositions utilizing such compounds.

BRIEF SUMMARY OF THE INVENTION

These and other objects and advantages of the invention are accomplished by providing novel compounds which are represented by the formula

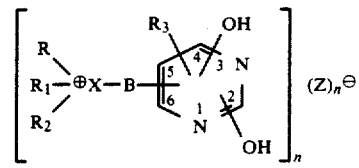

FORMULA A wherein X is N or P; B is a divalent linking group such as alkylene, preferably having from 1 to 6 carbon atoms, arylene, such as

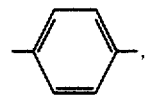

alkylarylene such as

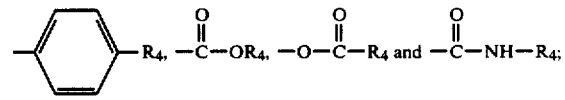

R and $R_2$ can independently be alkyl, preferably lower alkyl, substituted alkyl, cycloalkyl, aryl, aralkyl or alkaryl; $R_1$ can be alkyl, preferably lower alkyl, substituted alkyl, cycloalkyl, aryl, aralkyl, alkaryl or a divalent linking group such as, for example, any of the divalent linking groups recited above for B; or at least two of R, $R_1$ and $R_2$ together with X, can form a saturated heterocyclic ring system such as piperidine; or R, $R_1$ and $R_2$, together with X, can form an unsaturated heterocyclic ring system, such as pyridyl; $R_3$ can be hydrogen, alkyl, preferably having from 1 to 6 carbon atoms, substituted alkyl such as trifluoromethyl, aryl such as phenyl, nitro or halogen; $R_4$ is alkylene, preferably having from 1 to 6 carbon atoms; Z is an anion; and n is 1 or 2.

As is indicated above, a wide variety of quaternary nitrogen or phosphorous groups can be present in the compounds of the invention. The quaternary nitrogen or phosphorus atom can be substituted with alkyl groups such as methyl, ethyl, propyl, etc.; subtituted alkyl such as hydroxyethyl, hydroxypropyl, 3-(2-pyrrolidonyl)propyl, and acrylamidopropyl such as methylacrylamidopropyl; cycloalkyl groups such as cyclohexyl; aryl groups such as phenyl or naphthyl; aralkyl groups such as benzyl or phenethyl; alkaryl groups such as tolyl; or two or three of R, $R_1$ and $R_2$, together with the quaternary nitrogen or phosphorus atom, can form a substituted or unsubstituted, saturated or unsaturated heterocyclic ring system such as morpholino, piperidino, N'-formylpiperazino, 1-pyridyl, etc. As noted above, formation of a saturated, nitrogen or phosphorus-containing ring system will involve two of R, $R_1$ and $R_2$ whereas formation of an unsaturated ring system, e.g. 1-pyridyl, will involve each of R, $R_1$ and $R_2$. Further, it should be noted that where the compounds include two quaternary nitrogen or phosphorus groups, i.e., where n is 2, $R_1$ is a divalent linking group in order to attach the quaternary groups to each other.

A preferred quaternary group is 1-pyridyl. The 1-pyridyl group can be substituted at any of the available positions with any photographically acceptable substituent(s) which will not impair photographic processing. Typical suitable photographically acceptable substituents include, for example, alkyl, preferably having from 1 to 6 carbon atoms, carboxylic acid, carboxamide, etc. A particularly preferred group is 1-pyridyl substituted in the ortho position with a photographically acceptable substituent, preferably methyl.

The anion, Z, may be any photographically acceptable anion which will not impair photographic processing. Typical suitable anions include, for example, chloride, sulfate, tosylate, naphthalene sulfonate and the like.

The quaternary group can be connected, through the linking group, to the 2, 5 or 6 position of the pyrimidine residue. In the particularly preferred compounds of the invention the quaternary group is connected to the 6-position of the pyrimidine residue. It should be noted here that where the quaternary group is connected to the 5-position of the pyrimidine residue through a methylene linking group, the compound will undergo β-elimination in alkali and cleave. Thus, for photographic applications, where it is desired to use a compound having the quaternary group connected to the 5-position of the pyrimidine residue by an alkylene linking group, the latter should have two or more carbon atoms in order to prevent cleavage of the compound during photographic processing.

It should be noted here that when the linking group B is attached to the 5- or 6-positions of the pyrimidine residue the compounds may also be represented as follows:

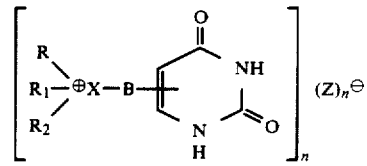

Both tautomeric forms of the compounds are intended to be encompassed by the generic Formula A.

DESCRIPTION OF THE PREFERRED EMBODIMENTS

Specific preferred compounds of the present invention are represented by the formulas

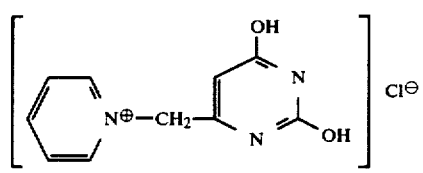

(I)

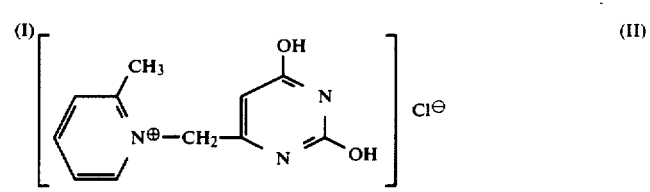

(II)

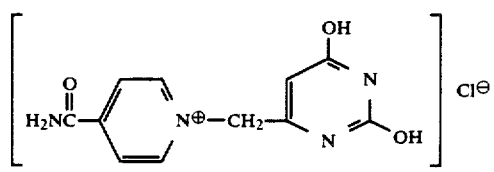

(III)

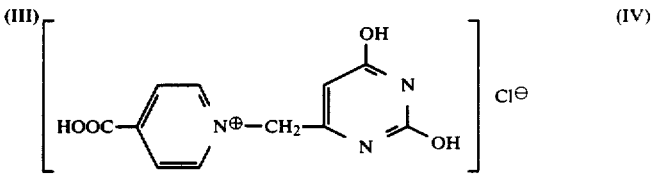

(IV)

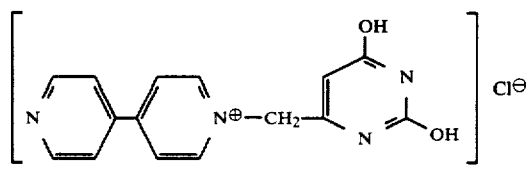

(V)

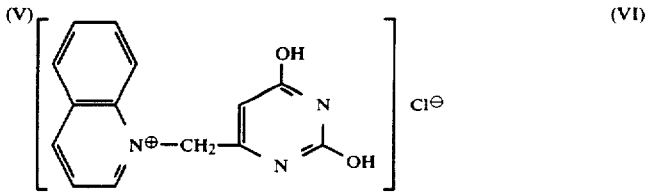

(VI)

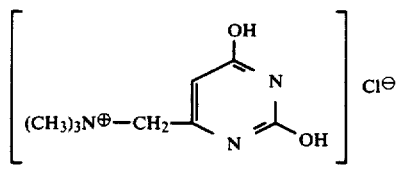

(VII)

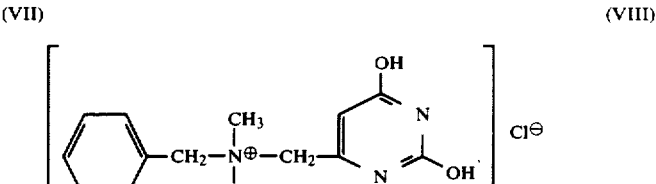

(VIII)

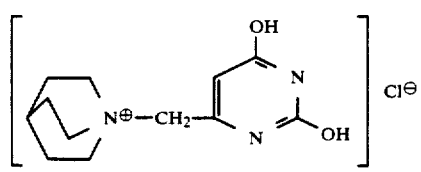

(IX)

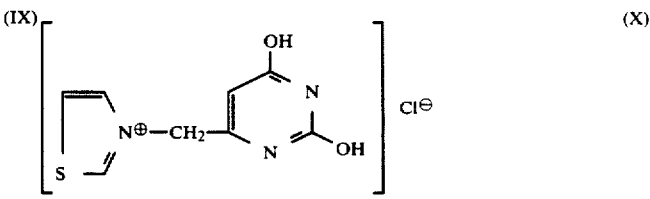

(X)

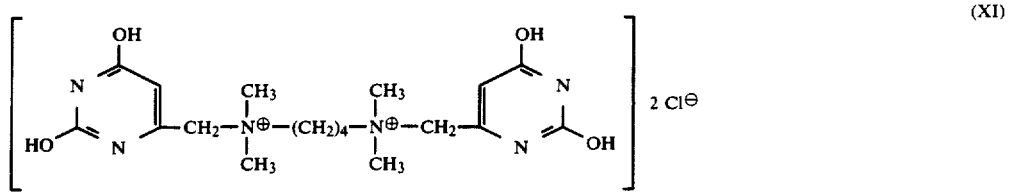
(XI)
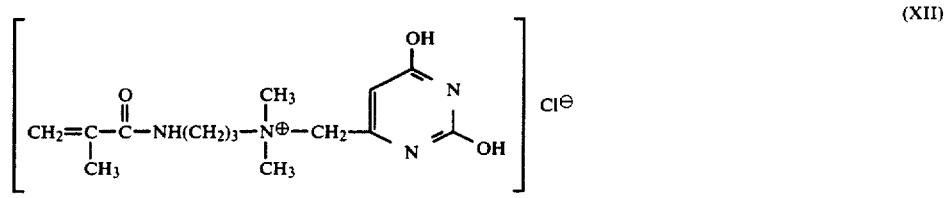
(XII)
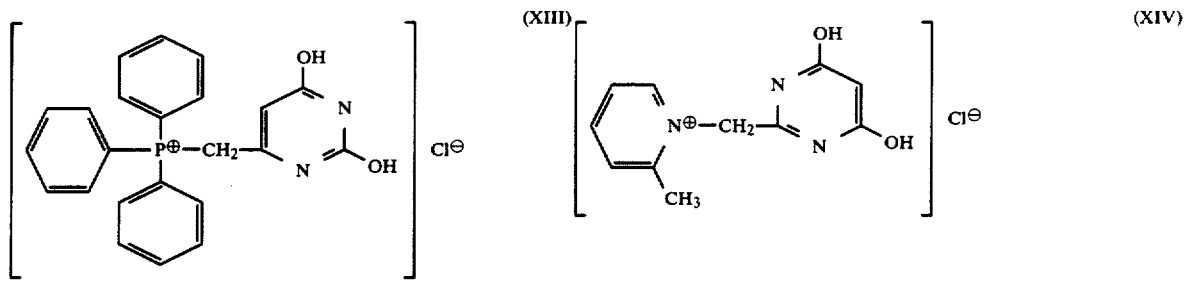
(XIII) (XIV)
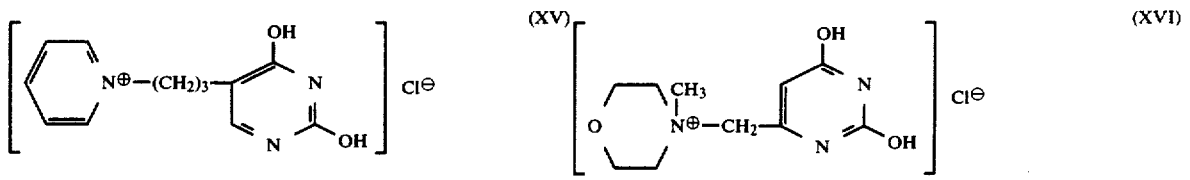
(XV) (XVI)
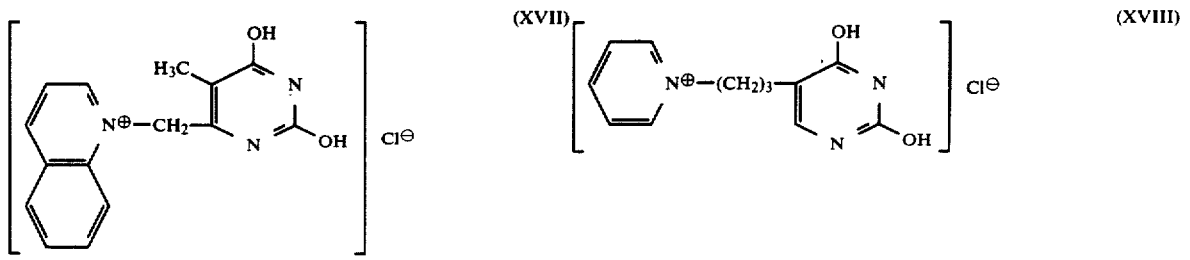
(XVII) (XVIII)
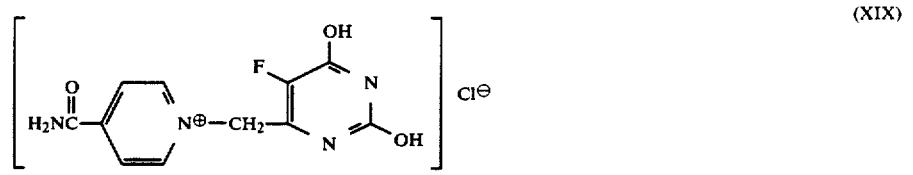
(XIX)
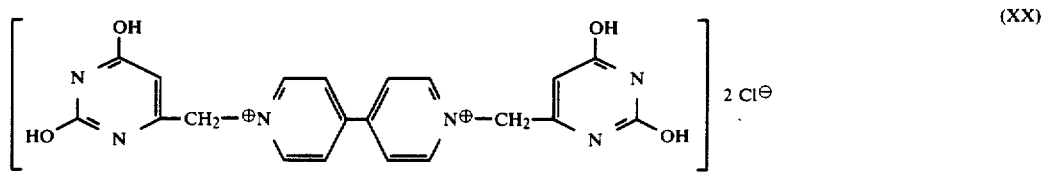
(XX)

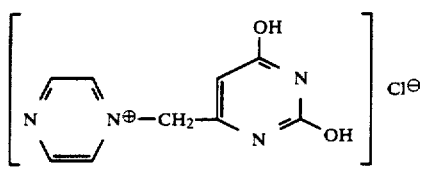

(XXI)

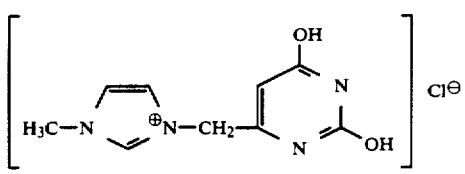

(XXIII)

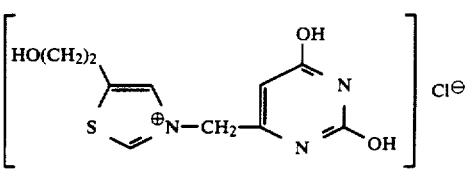

(XXII)

(XXIV)

The compounds of the invention can be prepared by reactions which are known in the art and these will be apparent from the following discussion as well as the specific examples provided below herein. Generally, the compounds can be prepared by reacting the appropriate substituted uracil, for example, chloromethyluracil with the appropriate quaternary, for example, pyridine or substituted pyridine, in a solvent such as dimethylformamide.

In formulating photographic processing compositions utilizing the above-described compounds, the compounds may be used singly or in admixture with each other or with other silver halide solvents. The total amount employed may vary widely depending upon the particular photographic system and should be used, for example, in a quantity sufficient for fixing a developed negative in conventional "tray" processing or in a quantity sufficient to give a satisfactory transfer print in diffusion transfer processes under the particular processing conditions employed.

Though the silver halide solvents of the present invention are broadly useful in a variety of photographic processes of the type in which water-soluble silver complexes are formed from the unreduced silver halide of a photoexposed and at least partially developed silver halide stratum, they find particular utility in diffusion transfer processes. A composition embodying the present invention specifically suitable for use in the production of transfer images comprises, in addition to the silver complexing agents of the above-described type, a suitable silver halide developing agent. Examples of developing agents that may be employed include hydroquinone and substituted hydroquinones, such as tertiary butyl hydroquinone, 2,5-dimethyl hydroquinone, methoxyhydroquinone, ethoxyhydroquinone, chlorohydroquinone; pyrogallol and catechols, such as catechol, 4-phenyl catechol and tertiary butyl catechol; aminophenols, such as 2,4,6-triamino-orthocresol; 1,4-diaminobenzenes, such a p-phenylenediamine, 1,2,4 triaminobenzene and 4-amino-2-methyl-N,N-diethylaniline; ascorbic acid and its derivatives, such as ascorbic acid, isoascorbic acid and 5,6-isopropylidene ascorbic acid, and other enediols, such as tetramethyl reductic acid; and hydroxylamines, such as N,N-di-(2-ethoxyethyl)hydroxylamine and N,N-di-(2-methoxyethoxyethyl)hydroxylamine.

In diffusion transfer processes, the processing composition, if it is to be applied to the emulsion by being spread thereon in a thin layer, also usually includes a viscosity-increasing reagent. The processing composition may comprise, for example, one or more silver halide solvents of the present invention, one or more conventional developing agents such as those enumerated above, an alkali such as sodium hydroxide or potassium hydroxide and a viscosity-increasing reagent such as a high molecular weight polymer, e.g., sodium carboxymethyl cellulose or hydroxyethyl cellulose.

In one such transfer process, the processing solution is applied in a uniformly thin layer between the superposed surfaces of a photoexposed photosensitive element and an image-receiving element, for example, by advancing the elements between a pair of pressure-applying rollers. The elements are maintained in superposed relation for a predetermined period, preferably for a duration of 15 to 120 seconds, during which exposed silver halide is reduced to silver and unreduced silver halide forms a water-soluble, complex salt which diffuses through the layer of solution to the image-receiving element, there to be reduced to an argental image. At the end of this period, the silver halide element is separated from the image-receiving element. Materials useful in such a transfer process are well known in the art.

The photosensitive element may be any of those conventionally used in silver diffusion transfer processes and generally comprises a silver halide emulsion carried on a base, e.g., glass, paper or plastic film. The silver halide may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers.

The image-receiving element preferably includes certain materials, the presence of which, during the transfer process has a desirable effect on the amount and character of silver precipitated on the image-receiving element. Materials of this type are known in the art.

Separating of the silver halide element from the image-receiving element may be controlled so that the layer of processing composition is removed from the image-receiving element or the layer of the processing composition is caused to remain in contact with the image-receiving element, e.g., to provide it with a protective coating. Techniques which enable such results to be accomplished as desired are described in U.S. Pat. No. 2,647,054. In general, the processing reagents are selected so that traces remaining after the solidified processing layer has been separated from the silver image or which remain in said layer adhered as a protective coating on the silver image, as indicated above, are colorless or pale, so as not to appreciably affect the appearance of the image and to have little or no tendency to adversely react with the silver image.

The silver halide solvents of the present invention also may be employed in diffusion transfer processes adapted to provide positive silver transfer images which may be viewed as positive transparencies without being separated from the developed negative silver image including such processes adapted for use in forming additive color projection positive images. Diffusion transfer processes of this type are known in the art. See, for example, U.S. Pat. Nos. 3,536,488, 3,615,428, and 3,894,871. The subject compounds also find utility in silver halide solvents in diffusion transfer processes utilizing the properties of the imagewise distribution of silver ions in the soluble silver complex made available in the undeveloped and partially developed areas of a silver halide emulsion to liberate a reagent, e.g., a dye in an imagewise fashion, as described in U.S. Pat. No. 3,719,489.

As noted above, in diffusion transfer film units the negative component comprising at least one photosensitive layer and the positive component comprising an image-receiving layer may be in separate sheet-like elements which are brought together during processing and thereafter either retained together as the final print or separated following image formation.

Rather than the photosensitive layer and the image-receiving layer being in separate elements, they may be in the same element. In one such film unit, the image-receiving layer is coated on a support and the photosensitive layer is coated on the upper surface of the image-receiving layer. The liquid processing composition is applied between the combined negative-positive element and a second sheet-like element or spreading sheet which assists in spreading the liquid composition in a uniform layer adjacent to the surface of the photosensitive layer.

Still other film units are those where the negative and positive components together may comprise a unitary structure wherein the image-receiving layer carrying the transfer image is not separated from the developed photosensitive layer(s) after processing but both components are retained together as a permanent laminate. Such film units include those for providing positive silver transfer images which may be viewed as positive color transparencies, such as, those described in U.S. Pat. No. 3,894,871. Other integral film units also include those adapted for forming a transfer image, in color or in black and white, viewable by reflected rather than by transmitted light. In addition to the aforementioned photosensitive layer(s) and image-receiving layer, such film units include means for providing a reflecting layer between the image-receiving and photosensitive layer(s) in order to mask the developed photosensitive layer(s) and to provide a white background for viewing the transfer image. This reflecting layer may comprise a performed layer of a reflecting agent included in the film unit or the reflecting agent may be provided subsequent to photoexposure, for example, by including the reflecting agent in the processing composition. In addition to these layers, the laminate usually includes dimensionally stable outer layers or supports, at least one of which is transparent so that the resulting transfer image may be viewed by reflection against the background provide by the light-reflecting layer. Integral negative-positive film units wherein the photosensitive and image-receiving layers are retained as a permanent laminate after processing are described, for example, in U.S. Pat. Nos. 3,415,644; 3,647,437 and 3,594,165.

It will be appreciated that in the formation of color transfer images, a dye image-providing material such as the compounds of U.S. Pat. No. 3,719,489 may be associated with the photosensitive silver halide layer or layers of the negative component.

The diffusion transfer film units described above are employed in conjunction with means, such as, a rupturable container containing the requisite processing composition and adapted upon application of pressure of applying its contents to develop the imagewise exposed film unit.

The invention will now be described in detail with respect to specific preferred embodiments thereof by way of examples, it being understood that these are intended to be illustrative only and the invention is not limited to the materials, process parameters, conditions etc., recited therein. All parts and percentages are by weight unless otherwise stated.

EXAMPLE I

A suspension of pyridine (24 ml, 0.3 m) and 6-chloromethyluracil (24.0 g, 0.15 m) in 150 ml of dimethylformamide was stirred at 110°–120° C. under dry nitrogen for one hour. After ten minutes a precipitate formed in the initial solution. The mixture was cooled in an ice bath and the solid collected, washed successively with dimethylformamide (sparingly), ethanol and ether and dried in air to give 34.9 g of Compound I, a colorless powder, m.p. 286°–287° C. (dec.).

$C_{10}H_{10}N_3O_2Cl$ requires 46.60% C, 4.66% H, 16.31% N, 18.64% O and 13.79% Cl. Elemental analysis found 46.57% C, 4.67% H, 16.28% N, 18.67% O and 13.93% Cl.

The structure of the compound was confirmed by IR and $^{13}C$ NMR spectra.

EXAMPLE II

A suspension of 6-chloromethyluracil (6.4 g, 0.04 m) and 2-picoline (8.1 ml, 0.08 m) in 20 ml of dimethylformamide was stirred at 100°–110° C. under nitrogen for two hours. The initial suspension became almost a complete solution after one hour followed by gradual formation of a thick precipitate. The mixture was cooled in an ice bath and the solid collected, washed successively with dimethylformamide (sparingly), 2-propanol and ether and dried in air to give 10.0 g of Compound II, a colorless powder, m.p. 291° C. (dec.)

$C_{11}H_{12}N_3O_2Cl$ requires 52.07% C, 4.73% H, 16.57% N, 12.62% O and 14.00% Cl. Elemental analysis found 51.89% C, 4.96% H, 16.55% N, 12.49% O and 14.01% Cl.

The structure of the compound was confirmed by IR and $^{13}C$ NMR spectra.

EXAMPLE III

A suspension of 6-chloromethyluracil (8.0 g, 0.05 m) and isonicotinamide (6.1 g, 0.05 m) in 50 ml of dimethylformamide was stirred under nitrogen for four hours at 120° C. Initially a clear solution formed which gave way to a colorless precipitate after about one-half hour. The reaction mixture was cooled and the precipitate collected, washed successively with dimethylformamide, ethanol and ethyl ether and dried in air to give 12.45 g (88% yield) of Compound III, a colorless powder, m.p. 317°–318° C. (dec.).

$C_{11}H_{11}N_4O_3Cl$ requires 46.73% C, 3.89% H, 19.82% N, 16.99% O and 12.57% Cl. Elemental analysis found 46.67% C, 4.12% H, 19.65% N, 17.16% O and 12.51% Cl.

The structure of the compound was confirmed by IR and $^{13}C$ NMR spectra.

EXAMPLE IV

A suspension of 6-chloromethyluracil (8.0 g, 0.05 m) and isonicotinic acid (6.15 g, 0.05 m) in 75 ml of dimethylformamide was stirred at 120° C. for four hours under nitrogen. The resulting mixture was cooled and the solid collected, washed successively with dimethylformamide, ethanol and ethyl ether and dried in air to give 10.98 g (77% yield) of Compound IV, a colorless solid, m.p. 297° C. (dec.).

$C_{11}H_{10}N_3O_4Cl$ requires 46.56% C, 3.53% H, 14.81% N, 22.57% O and 12.52% Cl. Elemental analysis found 46.21%, 3.81% H, 14.83% N, 22.77% O and 12.44% Cl.

The structure of the compound was confirmed by IR and $^{13}C$ NMR spectra.

EXAMPLE V

A suspension of 6-chloromethyluracil (8.03 g, 0.05 m) and 4,4'-bipyridine (3.91 g, 0.025 m) in 50 ml of dimethylformamide was stirred at 120°-130° C. under dry nitrogen. Within five minutes the suspension became a solution and almost immediately a precipitate formed which rapidly turned blue. Stirring was continued for about five hours. The reaction mixture was cooled and the solid collected, washed with dimethylformamide and then with ethyl ether and dried to give 7.88 g (99% yield) of Compound V, a blue powder, m.p. 327°-333° C. (dec.).

$C_{15}H_{13}N_4O_2Cl$ requires 56.88% C, 4.14% H, 17.69% N, 10.10% O and 11.19% Cl. Elemental analysis found 56.88% C, 4.20% H, 17.16% N, 12.28% O and 11.28% Cl.

The structure of the compound was confirmed by an IR spectrum.

EXAMPLE VI

Quinoline (12.92 g, 0.10 m) and 6-chloromethyluracil (8.03 g, 0.05 m) and 50 ml of dimethylformamide were stirred at 110°-120° C. under dry nitrogen for five hours. The reaction mixture was allowed to stand overnight. The orange precipitate was collected, washed sparingly with dimethylformamide and then with ethyl ether and dried to give 8.62 g of an orange powder which was resuspended in 100 ml of ethyl ether, collected and dried to give 7.39 g (51% yield) of Compound VI, an orange powder, m.p. 270° C. (dec.).

$C_{14}H_{12}N_3O_2Cl$ requires 58.04% C, 4.17% H, 14.50% N, 11.04% O, and 12.24% Cl. Elemental analysis found 57.90% C, 4.32% H, 14.39% N, 10.92% O and 12.35% Cl.

The structure of the compound was confirmed by an IR spectrum.

EXAMPLE VII

A mixture of chilled trimethylamine (50 g) and 6-chloromethyluracil (8.00 g, 0.05 m) in 50 ml of chilled dimethylformamide was stirred under dry nitrogen at 0° C. After about forty minutes a white precipitate formed. stirring was continued for about 3½ hours. The solid was collected, washed with anhydrous ether and dried in air to give 11.29 g of Compound VII.

$C_8H_{14}N_3O_2Cl.\frac{1}{2}H_2O$ requires 41.47% C, 6.67% H, 18.14% N, 18.42% O and 15.30% Cl. Elemental analysis found 41.55% C, 6.74% H, 18.09% N, 18.35% O and 15.34% Cl.

The structure of the compound was confirmed by IR and $^{13}C$ NMR spectra.

EXAMPLE VIII

A mixture of N,N-dimethylbenzylamine (20.0 g, 0.15 m) and 6-chloromethyluracil (16.06 g, 0.10 m) in 100 ml of dimethylformamide was stirred at 100° C. under dry nitrogen for one half hour. A thick precipitate formed. The reaction mixture was cooled and the solid collected, washed with dimethylformamide and then with ethyl ether, and dried in air to give 26.24 g (88% yield) of Compound VIII, a colorless powder, m.p. 254°-255° C. (dec.).

$C_{14}H_{18}N_3O_2Cl$ requires 56.85% C, 6.13% H, 14.21% N, 10.82% O and 11.99% Cl. Elemental analysis found 56.68% C, 6.19% H, 14.29% N, 11.05% O and 11.98% Cl.

The structure of the compound was confirmed by IR and $^{13}C$ NMR spectra.

EXAMPLE IX

To a solution of quinuclidine (10.0 g, 0.09 m) in 80 ml of dimethylformamide at 100° C. and under dry nitrogen, there was added, with stirring, 6-chloromethyluracil (14.44 g, 0.09 m). After one half hour the reaction mixture was cooled to 0° C. and the precipitate collected, washed with dimethylformamide and then with ethyl ether and dried in air to give 24.32 g (99% yield) of Compound IX, a colorless powder, m.p. 282°-283° C. (dec.).

$C_{12}H_{18}N_3O_2Cl$ requires 53.04% C, 6.68% H, 15.46% N, 11.78% O and 13.05% Cl. Elemental analysis found 52.97% C, 6.74% H, 15.52% N, 12.37% O and 12.54% Cl.

The structure of the compound was confirmed by IR and $^{13}C$ NMR spectrum.

EXAMPLE X

To a solution of thiazole (5.0 g, 0.058 m) in 50 ml of dimethylformamide at 110° C. and under dry nitrogen, there was added, with stirring, 6-chloromethyluracil (9.43 g, 0.058 m). Stirring was continued for 4 hours at 100°-110° C. The reaction mixture was cooled to 0° C. and the solid collected, washed with dimethylformamide and then with ethyl ether and dried in air to give 6.40 g (50% yield) of Compound X, a colorless powder, m.p. 274°-275° C. (dec.).

$C_8H_8N_3O_2SCl$ requires 39.11% C, 3.28% H, 17.10% N, 13.02% O, 13.05% S and 14.43% Cl. Elemental analysis found 38.99% C, 3.31% H, 17.02% N, 13.18% O, 13.00% S and 14.54% Cl.

The structure of the compound was confirmed by an IR spectrum.

EXAMPLE XI

A mixture of N,N,N',N'-tetramethyl-1,4-butanediamine (12.5 g, 0.087 m) and 6-chaloromethyluracil (27.82 g, 0.17 m) in 100 ml of dimethylformamide was stirred at 100° C. under dry nitrogen for one-half hour. The initial clear solution became a thick precipitate. The mixture was cooled and the solid collected, washed successively with dimethylformamide and ethyl ether and dried in air to give 38.87 g (94% yield) of compound XI, a cream colored powder, m.p. 241°–242° C. (dec.).

$C_{18}H_{30}N_6O_4Cl_2 \cdot \frac{1}{2}H_2O$ requires 45.57% C, 6.59% H, 17.72% N, 15.18% O and 14.95% Cl. Elemental analysis found 45.34% C, 6.83% H, 17.74% N, 15.13% O and 14.78% Cl.

The structure of the compound was confirmed by IR and $^{13}C$ NMR spectra.

EXAMPLE XII

A mixture of 6chloromethyluracil (16.0 g) and 1-N,N-Dimethylamino-3-methylacrylamidopropane (12.8 g) in about 50 ml of dimethylformamide was stirred overnight. The The resulting solid was collected and treated in accordance with the general procedure described previously to give 28 g of compound XII, a white solid, m.p. 208° C.

$C_{14}H_{23}N_4O_3Cl \cdot H_2O$ requires 48.21% C, 7.22% H and 16.06% N. Elemental analysis found 48.52% C, 7.1% H and 16.02% N.

EXAMPLE XIII

As a control a film unit was prepared wherein the negative element comprised a subcoated polyethylene terephthalate photographic film base on which the following layers were coated in succession:

1. as a polymeric acid layer approximately 9 parts of ½ butyl ester of polyethylene/maleic anhydride copolymer and 1 part of polyvinyl butyral coated at a coverage of about 26,460 mgs./m.²;
2. a timing layer comprising about 98.5% of a 60-29-6-4-0.4 pentapolymer of butylacrylate, diacetone acrylamide, methacrylic acid, styrene and acrylic acid and about 1.5% of gelatin coated at a coverage of about 3800 mgs./m.²;
3. a cyan dye developer layer comprising about 600 mgs./m.² of a cyan dye developer represented by the formula

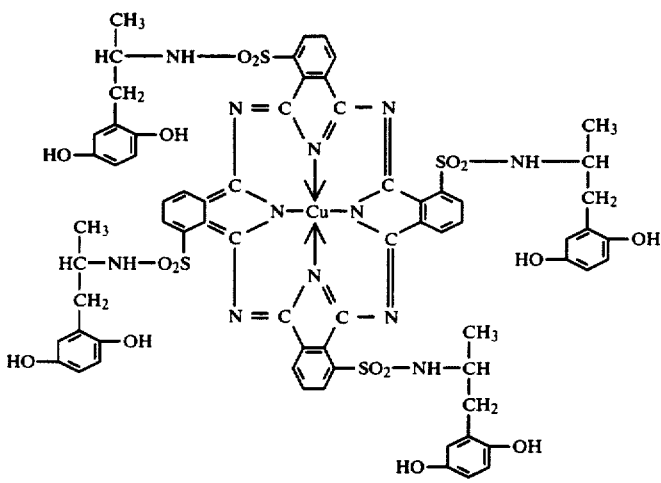

about 121 mgs./m.² of 4'-methyl phenyl hydroquinone, about 400 mgs./m.² of gelatin and about 225 mgs./m.² of dodecylaminopurine.

4. a reflection layer comprising about 1000 mgs./m.² of titanium dioxide, about 375 mgs./m.² of a polymeric latex of methacrylic acid, about 125 mgs./m.² of gelatin and about 375 mgs./m.² of the pentapolymer described in layer 2;

5. a red-sensitive silver iodobromide emulsion layer comprising about 1300 mgs./m.² of silver and about 780 mgs./m.² of gelatin;
6. an interlayer comprising about 3000 mgs./m.² of the pentapolymer described in layer 2, about 150 mgs./m.² of polyacrylamide and about 30 mgs./m.² of succinaldehyde;
7. a magenta dye developer layer comprising about 460 mgs./m.² of a magenta dye developer represented by the formula

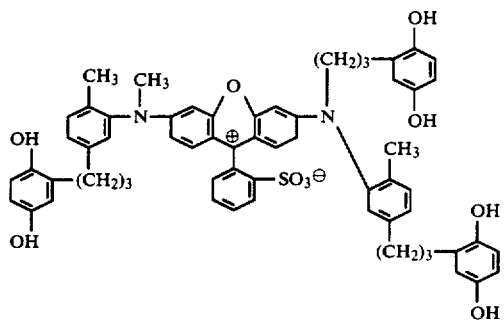

and about 275 mgs./m.² of gelatin;

8. a green-sensitive silver iodobromide emulsion layer comprising about 400 mgs./m.² of silver and about 176 mgs./m.² of gelatin;
9. an interlayer comprising about 2500 mgs./m.² of the pentapolymer described in layer 2, about 125 mgs./m.² of polyacrylamide, about 30 mgs./m.² of succindialdehyde and about 4 mgs./m.² of formaldehyde;
10. a layer comprising about 1000 mgs./m.² of gelatin and about 250 mgs./m.² of 2-phenylbenzimidazole;
11. a yellow dye developer layer comprising about 775 mgs./m.² of a yellow dye developer represented by the formula

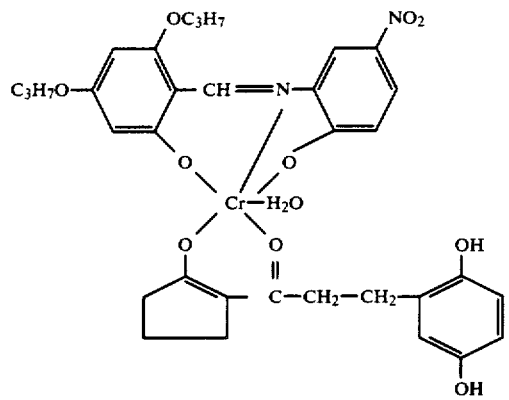

and about 310 mgs./m.² of gelatin;

12. a reflection layer comprising about 250 mgs./m.²

13. a blue-sensitive silver iodobromide emulsion layer comprising about 950 mgs./m.² of silver and about 475 mgs./m.² of gelatin;

14. a layer comprising about 250 mgs./m.² of 4'-methyl phenyl hydroquinone, about 110 mgs./m.² of gelatin and about 425 mgs./m.² of diethyldodecanamide;

15. a topcoat layer of gelatin coated at a coverage of about 484 mgs./m.².

The image-receiving element comprised a transparent subcoated polyethylene terephthalate film base upon which there was coated an image-receiving layer coated at a coverage of about 3229 mgs./m.² of a graft copolymer comprised of 4-vinylpyridine (4VP) and vinyl benzyl trimethylammonium chloride (TMQ) grafted onto hydroxyethyl cellulose (HEC) at a ratio HEC/4VP/TMQ of 2.2/2.2/1; and about 53.8 mgs./m.² of 1,4-butanediol diglycidyl ether.

The film unit was processed with a processing composition made up as follows:

| | WEIGHT PERCENT |
|---|---|
| Titanium dioxide | 47.47 |
| Oximated polydiacetone acrylamide | 0.66 |
| Potassium hydroxide | 4.50 |
| Benzothiazole | 1.45 |
| 4-hydroxypyrazolopyrimide | 0.07 |
| 4-aminopyrazolopyrimidine | 0.20 |
| 6-bromo-5-methyl-4-azabenzimidazole | 0.10 |
| Colloidal silica | 0.23 |
| N—phenethyl-α-picolinium bromide | 1.03 |
| Polyethylene glycol (MW 4000) | 0.37 |
| 3,5-dimethyl pyrazole | 0.16 |
| 2-methyl imidazole | 0.68 |
| 1-(4-hydroxy)phenylmercaptotetrazole | 0.04 |
| Nickel acetate | 0.29 |
| N—hydroxyethyl-N,N',N'—triscarboxymethyl ethylene diamine | 1.23 |
| Potassium thiosulfate | 0.08 |
| Citric acid | 0.10 |
| [structure with HOOC, NH—SO₂—C₁₆H₃₃—n] | 0.43 |
| [structure with C₁₈H₃₇O, OH, COOCH₃, H₃COOC, OH] | 1.47 |
| Water to make 100% | | of titanium dioxide, about 187.5 mgs./m.² of a polymeric latex of methacrylic acid and about 31 mgs./m.² of gelatin;

The negative element was exposed (0.5 meter-candle-second) on a sensitometer to a test scale with white light and then brought together with the image-receiving element and processed at 75° F. by passing the film unit through a pair of rollers at a gap spacing of about 0.0031 inch. The film unit was kept intact and viewed through the image receiving element.

Film Unit A according to the invention was prepared. It was identical to the control with the exceptions that the processing composition included 0.24% of Compound I and an additional 0.11% of potassium hydroxide (to compensate for the ionizable protons on Compound I). The film unit was processed as described above.

The neutral density columns of the images were read on a densitometer to obtain the Dmax and Dmin values for red, green and blue respectively. In addition the speeds of the red, green and blue curves respectively, (defined as the negative log of the relative exposure required to give red, green and blue absorption, respectively, in the neutral column a reflection density of 0.75) were measured. The values are shown in Table I.

TABLE I

|  |  | R | G | B | SPEED R | G | B |
|---|---|---|---|---|---|---|---|
| CONTROL | Dmax | 1.66 | 1.88 | 1.78 | 1.53 | 1.62 | 1.62 |
|  | Dmin | 0.14 | 0.13 | 0.16 |  |  |  |
| FILM UNIT A | Dmax | 1.55 | 1.67 | 1.71 | 1.66 | 1.77 | 1.71 |
|  | Dmin | 0.14 | 0.13 | 0.16 |  |  |  |

The film unit according to the invention exhibited an increase in all photographic speeds, with the largest increases being in the red and green speeds, without any greater than expected loss in Dmax.

EXAMPLE XIV

A control identical to that described in Example XIII was processed as described therein. Film unit B, which was identical to the control with the exceptions that the processing composition included 0.13% of Compound II and an additional 0.08% of potassium hydroxide (to compensate for the ionizable protons on Compound II) was processed in the same way. The photographic responses of the film units is shown in Table II

TABLE II

|  |  | R | G | B | SPEED R | G | B |
|---|---|---|---|---|---|---|---|
| CONTROL | Dmax | 1.86 | 1.99 | 1.79 | 1.47 | 1.55 | 1.52 |
|  | Dmin | 0.16 | 0.15 | 0.17 |  |  |  |
| FILM UNIT B | Dmax | 1.76 | 1.84 | 1.74 | 1.58 | 1.67 | 1.58 |
|  | Dmin | 0.15 | 0.13 | 0.18 |  |  |  |

Again, the film unit according to the invention exhibited an increase in all photographic speeds, with the largest increases being in the red and green speeds, without any greater than expected loss in Dmax.

Although the invention has been described in detail with respect to various preferred embodiments thereof, these are intended to be illustrative only and the invention is not limited thereto but rather those skilled in the art will recognize that modifications and variations may be made therein which are within the spirit of the invention and the scope of the appended claims.

What is claimed is:

1. A photographic product comprising a support, a silver halide emulsion carried on said support and a compound represented by the formula

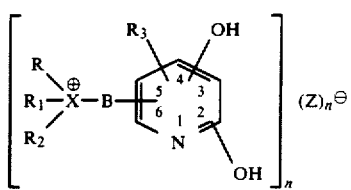

wherein X is nitrogen or phosphorus; B is a divalent linking group; R and $R_2$ are independently selected from the group consisting of alkyl, substituted alkyl, cycloalkyl, aryl, aralkyl and alkaryl; $R_1$ is selected from the group consisting of alkyl, substituted alkyl, cycloalkyl, aryl, aralkyl, alkaryl and a divalent linking group; or at least two of R, $R_1$ and $R_2$, together with X, form a substituted or unsubstituted heterocyclic ring; $R_3$ is selected from the group consisting of hydrogen, alkyl, substituted alkyl, aryl, nitro and halogen; Z is a photographically acceptable anion; and n is 1 or 2.

2. A photographic product as defined in claim 1 wherein X is nitrogen.

3. A photographic product as defined in claim 2 wherein R, $R_1$ and $R_2$, together with X, form a

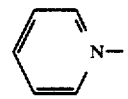

group.

4. A photographic product as defined in claim 3 wherein B is methylene.

5. A photographic product as defined in claim 4 wherein $R_3$ is hydrogen and n is 1.

6. A photographic product as defined in claim 2 wherein R, $R_1$ and $R_2$, together with X, form a

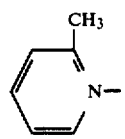

group, B is methylene, $R_3$ is hydrogen and n is 1.

7. A photographic product as defined in claim 1 wherein said compound is represented by the formula

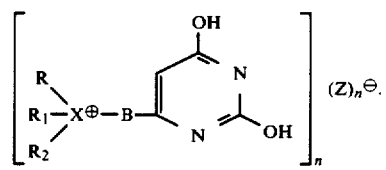

8. A photographic product as defined in claim 7 wherein R, $R_1$ and $R_2$, together with X, form a

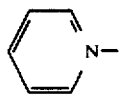

group, B is methylene and n is 1.

9. A photographic product as defined in claim 7 wherein R, $R_1$ and $R_2$, together with X, form a

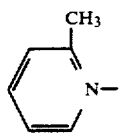

group, B is methylene and n is 1.

10. A diffusion transfer photographic process comprising:
(1) reacting exposed silver halide of an imagewise exposed photosensitive silver halide emulsion layer carried on a support with a silver halide developing agent in aqueous alkaline solution;
(2) reacting unreduced silver halide of said photosensitive emulsion with a compound represented by the formula

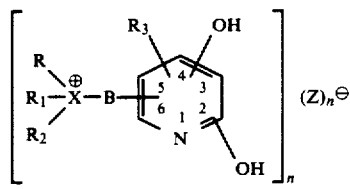

wherein X is nitrogen or phosphorus; B is a divalent linking group; R and $R_2$ are independently selected from the group consisting of alkyl, substituted alkyl, cycloalkyl, aryl, aralkyl and alkaryl; $R_1$ is selected from the group consisting of alkyl, substituted alkyl, cycloalkyl, aryl, aralkyl, alkaryl and a divalent linking group; or at least two of R, $R_1$ and $R_2$, together with X, form a substituted or unsubstituted heterocyclic ring; $R_3$ is selected from the group consisting of hydrogen, alkyl, substituted alkyl, aryl, nitro and halogen; Z is a photographically acceptable anion; and n is 1 or 2; said compound being capable of reacting with silver halide to form a complex silver salt that is soluble in said alkaline solution;
(3) transferring said complex silver salt to a superposed image-receiving layer; and
(4) reducing said transferred complex silver salt to provide a silver image.

11. The process as defined in claim 10 wherein X is nitrogen.

12. The process as defined in claim 11 wherein R, $R_1$ and $R_2$, together with X, form a

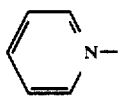

group.

13. The process as defined in claim 12 wherein B is methylene.

14. The process as defined in claim 13 wherein $R_3$ is hydrogen and n is 1.

15. The process as defined in claim 11 wherein R, $R_1$ and $R_2$, together with X, form a

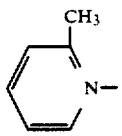

group, B is methylene, $R_3$ is hydrogen and n is 1.

16. The process as defined in claim 10 wherein said compound is represented by the formula

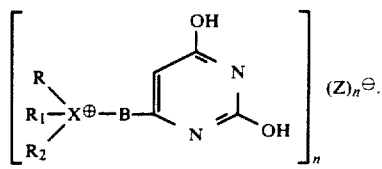

17. The process as defined in claim 16 wherein R, $R_1$ and $R_2$, together with X, form a

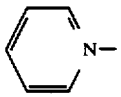

group, B is methylene and n is 1.

18. The process as defined in claim 16 wherein R, $R_1$ and $R_2$, together with X, form a

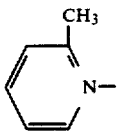

group, B is methylene and n is 1.

19. A photographic processing composition comprising an aqueous alkaline solution containing a viscosity-increasing polymer and at least one compound represented by the formula

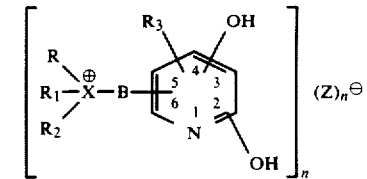

wherein X is nitrogen; B is methylene; R, $R_1$ and $R_2$, together with X, form a

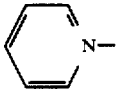

group; $R_3$ is selected from the group consisting of hydrogen, alkyl, substituted alkyl, aryl, nitro and halogen; Z is a photographically acceptable anion; and n is 1 or 2.

20. A composition as defined in claim 19 wherein $R_3$ is hydrogen and n is 1.

21. A photographic processing composition comprising an aqueous alkaline solution containing a viscosity-increasing polymer and at least one compound represented by the formula

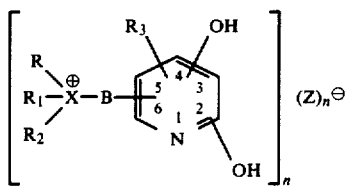

wherein X is nitrogen; B is methylene; R, $R_1$ and $R_2$, together with X, form a

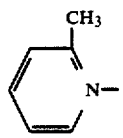

group; $R_3$ is hydrogen; Z is a photographically acceptable anion; and n is 1.

22. A photographic processing composition comprising an aqueous alkaline solution containing a viscosity-increasing polymer and at least one compound represented by the formula

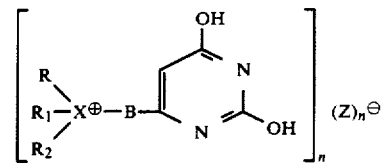

wherein X is nitrogen or phosphorous; B is a divalent linking group; R and $R_2$ are independently selected from the group consisting of alkyl, substituted alkyl, cycloalkyl, aryl, aralkyl and alkaryl; $R_1$ is selected from the group consisting of alkyl, substituted alkyl, cycloalkyl, aryl, aralkyl, alkaryl and a divalent linking group; or at least two of R, $R_1$ and $R_2$, together with X, form a substituted or unsubstituted heterocyclic ring; $R_3$ is selected from the group consisting of hydrogen, alkyl, substituted alkyl, aryl, nitro and halogen; Z is a photographically acceptable anion; and n is 1 or 2.

23. A composition as defined in claim 22 wherein R, $R_1$ and $R_2$, together with X, form a

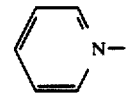

group, B is methylene and n is 1.

24. A composition as defined in claim 22 wherein R, $R_1$ and $R_2$, together with X, form a

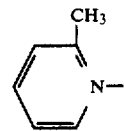

group, B is methylene and n is 1.

* * * * *

UNITED STATES PATENT AND TRADEMARK OFFICE
CERTIFICATE OF CORRECTION

PATENT NO. : 4,713,313

DATED : December 15, 1987

INVENTOR(S) : James R. Bartel-Keith, deceased, et al.

It is certified that error appears in the above-identified patent and that said Letters Patent is hereby corrected as shown below:

Claim 1, col. 18, lines 1-10, delete the formula and replace it with

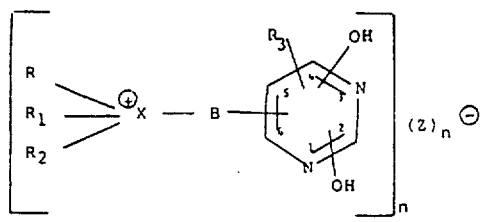

Claim 10, col. 19, lines 21-30, delete the formula and replace it with

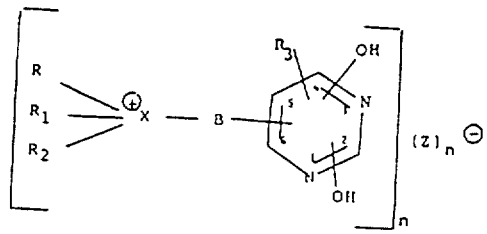

UNITED STATES PATENT AND TRADEMARK OFFICE
CERTIFICATE OF CORRECTION

PATENT NO. : 4,713,313

DATED : December 15, 1987

INVENTOR(S) : James R. Bartels-Keith, deceased, et al.

It is certified that error appears in the above—identified patent and that said Letters Patent is hereby corrected as shown below:

Claim 19, col. 20, lines 45-53, delete the formula and replace it with

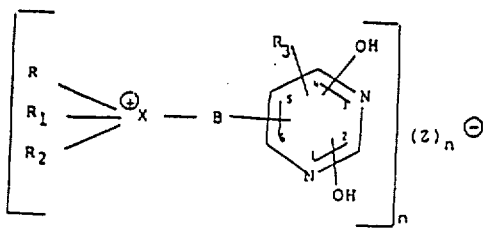

Claim 21, col. 21, lines 10-19, delete the formula and replace it with

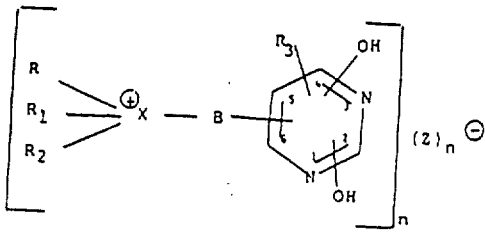

Signed and Sealed this

Twenty-first Day of June, 1988

Attest:

DONALD J. QUIGG

Attesting Officer

Commissioner of Patents and Trademarks